US007029498B2

(12) United States Patent
Boehm et al.

(10) Patent No.: US 7,029,498 B2
(45) Date of Patent: *Apr. 18, 2006

(54) VARIABLE HEIGHT VERTEBRAL IMPLANT

(75) Inventors: Heinrich Boehm, Weimar (DE); Thomas Busch, Bad Blankenburg (DE); Erich Orschler, Kirchenpingarten (DE)

(73) Assignee: Koenigsee Implantate und Instrumente zur Osteosynthese GmbH, Koenigsee/Aschau (DE)

(*) Notice: Subject to any disclaimer, the term of this patent is extended or adjusted under 35 U.S.C. 154(b) by 185 days.

This patent is subject to a terminal disclaimer.

(21) Appl. No.: 10/240,268

(22) PCT Filed: Mar. 29, 2001

(86) PCT No.: PCT/EP01/03611

§ 371 (c)(1),
(2), (4) Date: Feb. 21, 2003

(87) PCT Pub. No.: WO01/72246

PCT Pub. Date: Oct. 4, 2001

(65) Prior Publication Data

US 2003/0163199 A1 Aug. 28, 2003

(30) Foreign Application Priority Data

Mar. 31, 2000 (DE) .......................... 200 05 958 U

(51) Int. Cl.
*A61F 2/44* (2006.01)

(52) U.S. Cl. ............................... 623/17.11; 623/17.15; 623/17.16; 606/90

(58) Field of Classification Search ............ 623/17.11, 623/17.15, 17.16; 606/90
See application file for complete search history.

(56) References Cited

U.S. PATENT DOCUMENTS 4,401,112 A * 8/1983 Rezaian ....................... 606/61
4,502,160 A 3/1985 Moore et al.
5,290,312 A 3/1994 Kojimoto et al.
5,405,391 A 4/1995 Hednerson et al.
6,190,414 B1 * 2/2001 Young et al. ............ 623/17.15
6,200,348 B1 * 3/2001 Biedermann et al. .... 623/17.11
6,419,705 B1 * 7/2002 Erickson .................. 623/17.16
6,436,140 B1 * 8/2002 Liu et al. ................. 623/17.11
6,610,090 B1 * 8/2003 Bohm et al. ............. 623/17.11

(Continued)

FOREIGN PATENT DOCUMENTS

DE 30 23 942 1/1982

(Continued)

*Primary Examiner*—Corrine McDermott
*Assistant Examiner*—Javier G. Blanco
(74) *Attorney, Agent, or Firm*—Oblon, Spivak, McClelland, Maier & Neustadt, P.C.

(57) ABSTRACT

A height-variable vertebral body implant having a first, essentially U-shaped or C-shaped cage, and vertebral support surfaces formed on the first cage. The first cage is an inner cage, which is embraced and guided in a telescopic manner by a second, outer U-shaped or C-shaped cage. Further, legs of the inner and the outer cage are aligned such that a continuous lateral opening is obtained, and the inner and the outer cages are mutually fixed in a predetermined final position. The inner cage includes in an area of a part connecting the legs a longitudinally extending elongated hole having a unilateral toothing. In cooperation with an instrument including a complementary toothing, a relative movement and adjustment may be effected between the cages. In addition, a thread bore is formed in the outer cage in a position below the area of the elongated hole to fix a desired adjustment position.

16 Claims, 11 Drawing Sheets

43
42
37
44
32

U.S. PATENT DOCUMENTS 6,752,832 B1 * 6/2004 Neumann ................ 623/17.15

FOREIGN PATENT DOCUMENTS

DE 198 03 700 8/1999
EP 0 832 622 4/1998
JP 2000210315 A * 8/2000
JP 2005160875 A * 6/2005
WO 92 01428 2/1992

* cited by examiner

Ansicht B
14
12
13
Modul 0,5

B
4
2
2
1
Y
A
A
45
Y 5:1
10
16
3
3
X
10
X 5:1

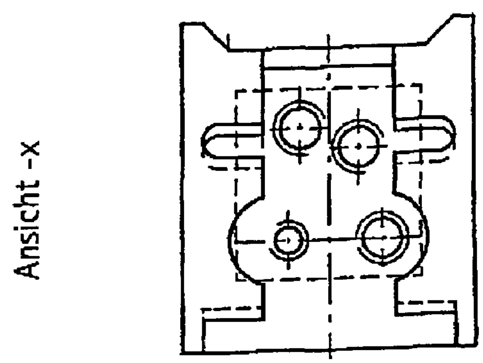
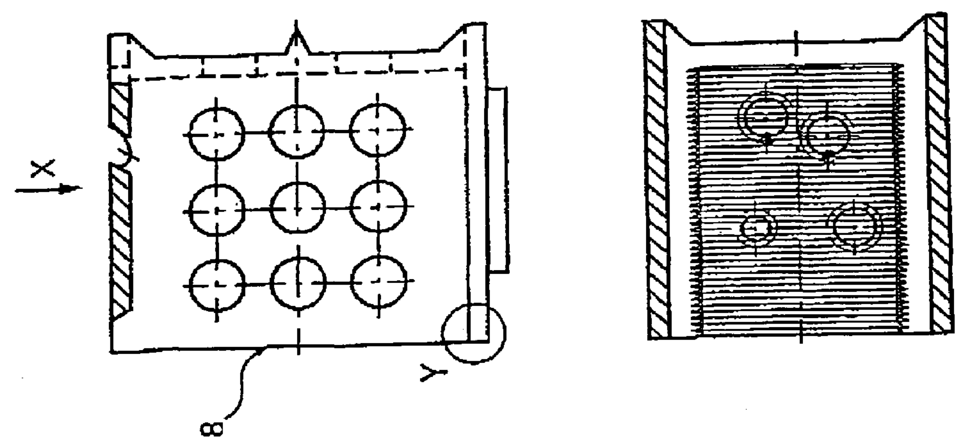
Fig. 3
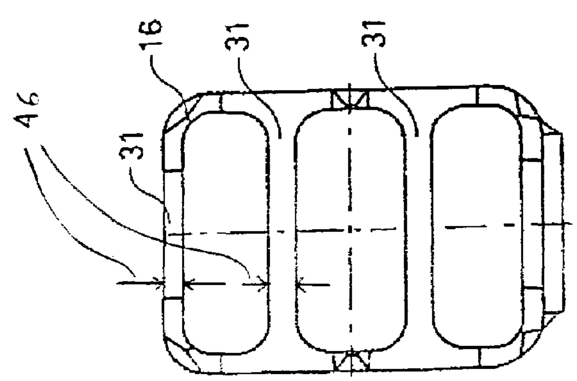

2
4
4
31
8

2
2
1
47
31
48
14
11
12
13

36
33
32
34
X 2:1
35
32
33
X

VARIABLE HEIGHT VERTEBRAL IMPLANT

BACKGROUND OF THE INVENTION

1. Field of the Invention

The invention relates to a height-variable vertebral body implant according to the preamble of claim 1, as well as to an actuating instrument set for same.

2. Description of Related Art

From DE 43 28 062 A1 a supporting bar with laterally slide-on implant bodies is known. In order to enable a sliding-on, the implant bodies are provided with a lateral groove, with a surface structure in the form of a toothing serving to fix the surfaces of the implant bodies to one another and, in addition, to maintain the position with respect to the vertebral body or bodies.

Due to the fact that the implant bodies shown therein are pre-manufactured with various heights and can be slid onto the bar, a certain height adaptation can be effected. However, the handling of the implant is extremely difficult, and the manufacturing costs are high.

From EP 0 302 719 a U-shaped implant is known wherein openings are provided which serve to introduce bone cement. Further openings may be provided for accommodating a screw in order to secure the implant immediately in the vertebra. Carbon-fiber reinforced synthetic material is specified for the shown implant.

The implant placeholder according to EP 0 268 115 A1 comprises a cylinder jacket element with a plurality of rhomboidal reticulate recesses. A ring provided therein at the upper and lower end of the cylinder jacket element prevents an undesired excessively deep penetration of the implant into the vertebra. An additionally provided base plate serves the same purpose. The cylinder jacket element is closed and has no further openings apart from the rhomboidal openings for the introduction of bone cement, so that in this case, too, there are difficulties in the surgical handling with disadvantages in the injection of bone cement.

DE 196 15 938 A1 discloses a vertebral column supporting device for carrying out an intersomatic arthrodesis. The supporting device consists of titanium, has a plane and elongated shape with an expansion in its central area. The edges with the exception of the central area are provided with a saw tooth profile. The shape of the presented supporting device is similar to that of an open ring, with the supporting device being adaptable with respect to its diameter to various applications by means of bending up the end portions of the supporting device.

A height-variable vertebral body substitution with a sleeve and with a first counter-bearing body which is displaceable in an axial direction or a second counter-bearing, respectively, is known from DE 44 09 392 A1. For moving the counter-bearing bodies relative to each other, a threaded means is provided. A similar principle is shown in DE 44 23 257 A1.

An adjustability via a thread is also mentioned in DE 195 19 101 A1, wherein tooth-shaped recesses are provided at the ends of the sleeve portions of the vertebral body substitution, in order to realize a radial locking relative to the vertebrae. The cylindrical portions of the vertebral body substitution have a plurality of recesses in order to improve the growing through with body material. The implantation of the vertebral body substitution according to DE 195 19 101 A1, however, is extremely critical because a corresponding spreading apart of the vertebrae must be effected for this purpose. In addition, the metal mass of the known implant is too great, with the corresponding, disadvantageous post-operative consequences.

DE 195 09 317 A1 shows an implant intended for being implanted as a placeholder between vertebral bodies of the vertebral column, with two end-located plate-shaped implant parts being provided interacting with an intermediate central implant part, which is rotatably connected with the end-located plate-shaped implant part. The shown implant parts are configured as tubular sleeves or as frontal rings. Bone cement may be introduced through provided openings. These openings, however, are only then optimally suited for being charged with bone cement, when they are brought to coincide, which, however, is problematical with the chosen adjusting principle.

With respect to the adjustability, reference is also made to the document U.S. Pat. No. 5,236,460, which shows a telescopic arrangement of an implant, wherein a curing material can be introduced into the telescopic space by means of a special tool. The document EP 0 637 439 A1, on the other hand, shows an implant including a wedge gear for the height adjustment. In addition, locking teeth can in this case be pivoted out so as to claw the implant between the vertebrae after its placement.

The document U.S. Pat. No. 5,290,312 concerns a height-variable vertebral body implant having two U-shaped cages with the inner cage being embraced and guided by the outer cage. The therein shown cages, however, are fixed point-wise and only unilaterally in the vertebra via screws. Moreover, for the spreading-apart operation, a forceps or similar instrument must be used, since the implant itself does not feature any such adjustment means, so that minimally invasive surgeries are not possible.

SUMMARY

Taking the indicated prior art into consideration, the object of the invention consists in proposing a further developed height-variable vertebral body implant, as well as an actuating instrument set for same, which features an excellent stability with a minimum amount of material, and which is not only applied as a usual placeholder but which may also be used for spreading apart vertebrae and for permanently correcting abnormal postures, so that the surgical handling is very simple. Moreover, the vertebral body implant is intended to have optimized openings for the introduction of bone cement, whereby the fusion, as well, has to be guaranteed. The implant is also intended to be suited for minimally invasive surgeries.

The task of the invention is solved by a subject matter according to the definition as per claim 1, with the dependent claims comprising at least appropriate configurations and advanced developments.

The invention is comprised of the claim-wise defined feature combination, in that the front sides of the cages guided within each other have integral vertebral support surfaces, as well as tooth-like locking projections extending in the longitudinal direction. Hereby, said projections, while locking the implant, penetrate into the vertebral surface, too deep a penetration with the consequence of a bone destruction, however, being prevented by the tongue-like or continuous vertebral support surfaces. Inwardly directed curved portions of the inner and outer cage result in an essential stability increase and prevent the otherwise open U-shaped or C-shaped cages from yielding to buckling.

The specific adjustment means according to the invention is inventive. For this purpose, the inner cage has, preferably in the area of the part connecting the legs, an elongated hole extending in the longitudinal direction and including a toothing. In cooperation with a specific instrument comprising a complementary toothing, a relative movement and an adjustment of the cages relative to each other may be achieved in this case. In surgical use, the implant is placed with, the cage telescoped back, the introduction of the instrument allowing the desired spreading apart but also the retraction. When the end position has been reached, this position is fixed by means of at least one locking screw.

For this purpose, a second elongated hole is provided in the inner cage adjacent to the first elongated hole.

With the inventive subject matter such as described above, a first, inner cage is embraced and guided by a second, outer U-shaped cage. The legs of the inner and the outer cage are aligned in such a manner that a continuous lateral opening is obtained. This continuous lateral opening faces the surgeon during the operation and enables both the introduction of the tool for the described height-adjustment or the locking operation, as well as the optimal placement of bone cement.

According to a further concept, the cages have vertebral support surface webs each mounted on the top of the inner cage or the base of the outer cage. These webs are configured in such a manner that they can also be separated by the surgeon or parts of it can be detached by him.

On the manufacturing side, the milling/erosion technology is preferably applied, so that the stability of the implant increases.

It is to be noted that the term U-shaped has also to be understood as a polygon shape, a semi-circular or circular cylindrical shape or the like, i.e. that which matters for the inventive cages is the possibility of the telescopic guidance inside one another and the mutual support of the side walls, whereby it is ensured that a continuous lateral opening is obtained.

With the inventive subject matter such as described above, one hence starts from a first, inner cage that is embraced and guided by a second, outer U-shaped cage. The legs of the inner and the outer cage are aligned in such a manner that a continuous lateral opening is obtained. This continuous lateral opening faces the surgeon during the operation and enables both the introduction of the tool for the described height-adjustment or the locking operation, respectively, as well as the optimal placement of bone cement.

In order to increase the stability of the vertebral implant, the legs of the inner and the outer cage each comprise on their leg ends an inwardly directed curved portion. Hereby, in spite of the mentioned continuous lateral opening, the desired predetermined positional coordination is maintained upon the action of pressure forces and/or rotational forces without necessitating further stabilizing means.

In addition, there is the possibility that at least in the area of the curved portions of the mutually opposite surfaces of the cages, a preferably punched locking toothing is present so as to preclude any displacement or undesired rotation of the cages relative to each other.

In the area of that part of the U-shaped or C-shaped cages, which connects the legs, bores for accommodating at least one locking screw are arranged, with the corresponding bore of the outer cage comprising a thread.

The height-variability of the vertebral body implant, as explained, is realized in a preferred embodiment in that the inner cage, preferably in the area of that part connecting the legs, comprises a first elongated hole extending in the longitudinal direction and comprising a toothing, so as to achieve, in cooperation with the instrument, a relative movement and a corresponding adjustment between the cages. A further, second elongated hole is preferably provided adjacent to the first elongated hole, and serves for locking or intermediately fixing the adjustment position by means-of a locking screw.

In order to facilitate the penetration of the locking projections until the abutment of the vertebral support surfaces relative to the neighboring vertebrae without causing serious bone damages, the locking projections, which are, for example, of a triangular shape, are ground to a cutting edge.

The locking projections and vertebral support surfaces or webs, which are each provided on one of the front faces of the first and the second cage, are purposefully arranged in an alternating manner so as to ensure the desired planar position of the implant.

The material for the cages is preferably selected in a manner that a certain residual elasticity remains maintained which comes close to the properties of the vertebral bones, so that a favorable bone growth is given.

In one embodiment of the invention, the cages may be configured to be stackable via a connecting part. In this case, the possibility exists of providing, starting from an in turn specific middle part, cages which can be telescoped on both sides.

The base surfaces and/or cover surfaces of the cages may feature an angular position or form deviating from the parallel line and adapted to the anatomic conditions.

In shaping, there exists the possibility of configuring the cages in a curved shape, which are then adjustable along a ring segment guiding path.

Normally, a locking of the implant by its spreading apart relative to the respective neighboring vertebrae bodies is sufficient; however, the possibility is provided to additionally anchor the implant, e.g. by screws, so that all forces arising with the natural movement of the human body, may be safely accommodated.

The inventive actuating instrument set for the presented height-variable vertebral body implant comprises a longitudinally extended guidance rod having a thread end. The instrument having an outer toothing is configured with a hollow cylinder for receiving the guidance rod, and on the end opposite the toothing, a handle comprising a knurled screw acting upon the guidance rod.

In addition, a gripping forceps is provided having clamping jaws engaging in corresponding recesses that are provided on the implant cages.

Navigation aids may be mounted on the gripping forceps for positional or image identification. Likewise, means for an easier positioning of a screw driver including a screw holder and/or the guidance rod may be arranged.

By means of the implant and the actuating instrument set, an endoscopically assisted placement of the implant is possible in a minimally invasive surgical procedure. The patient is in a prone position with a surgical access ensuing via the respective spread-apart ribs.

The implant is prepared as follows. First, at least one locking screw is introduced in the at least one thread bore provided in the outer cage. In this case, that bore is chosen that is located in the zone of a further, second elongated hole formed in the inner cage. This locking screw, however, remains loose for the time being, so that the desired displaceability of the cages is maintained, Then, the guidance rod is inserted in the thread bore of the outer cage, and namely into that situated in a position below the zone of the first elongated hole. Subsequently, the instrument having the outer toothing is slid over the guidance rod, and, thereupon, the rotatory movement is converted into a translatory movement by a rotation of the handle and an engagement of the toothing.

With the cage telescoped back and employing the gripping or holding forceps, the implant may then be placed. A corresponding representation on the gripping forceps indicates the extension direction of the gripping forceps, and hence the cranial implantation side, as well. The implant hence may be integrated in the above-described meaning into the corporectomide effect, and may there be correspondingly aligned relative to the body axis. Through the spreading-apart by means of the instrument including the outer toothing, the implant is then fixed and the securing operation of the respective height position is then effected via the knurled screw present on the instrument, so as to subsequently tighten the at least one locking screw by means of a screw driver.

In a preferred embodiment, the screws used or to be inserted are provided in different colors, preferably red, yellow and green, so as to predetermine an actuating sequence through this resulting traffic light function and to preclude confusions.

It is sometimes beneficial to provide not only one but several locking screws. Also, it is reasonable to provide an identification marking on the guidance rod enabling the surgeon to identify the exact position of the instrument including the toothing, so as to preclude an undesired shearing-off or a damage of elongated hole/toothing section. For this purpose, the handle of the instrument may be configured as a continuous extension of the hollow-cylindrical shape, and a notch or the like may be formed on the guidance rod, which exits from the handle end with the nominal position so that the guidance rod becomes visible or palpable.

It has turned out that surprisingly, the tooth-like locking projection, but likewise the vertebral support surfaces sufficiently secure the implant against the forces acting during the tightening of the locking screws.

In the following, the invention will be explained in more detail with reference to an exemplary embodiment, as well as by means of the Figures.

BRIEF DESCRIPTION OF THE DRAWINGS

FIGS. 3; 4 a second embodiment of an outer cage and an inner cage in various views, comprising webs of the same dimensions as vertebral support surfaces;

DETAILED DESCRIPTION OF THE DRAWINGS

Figure 1:
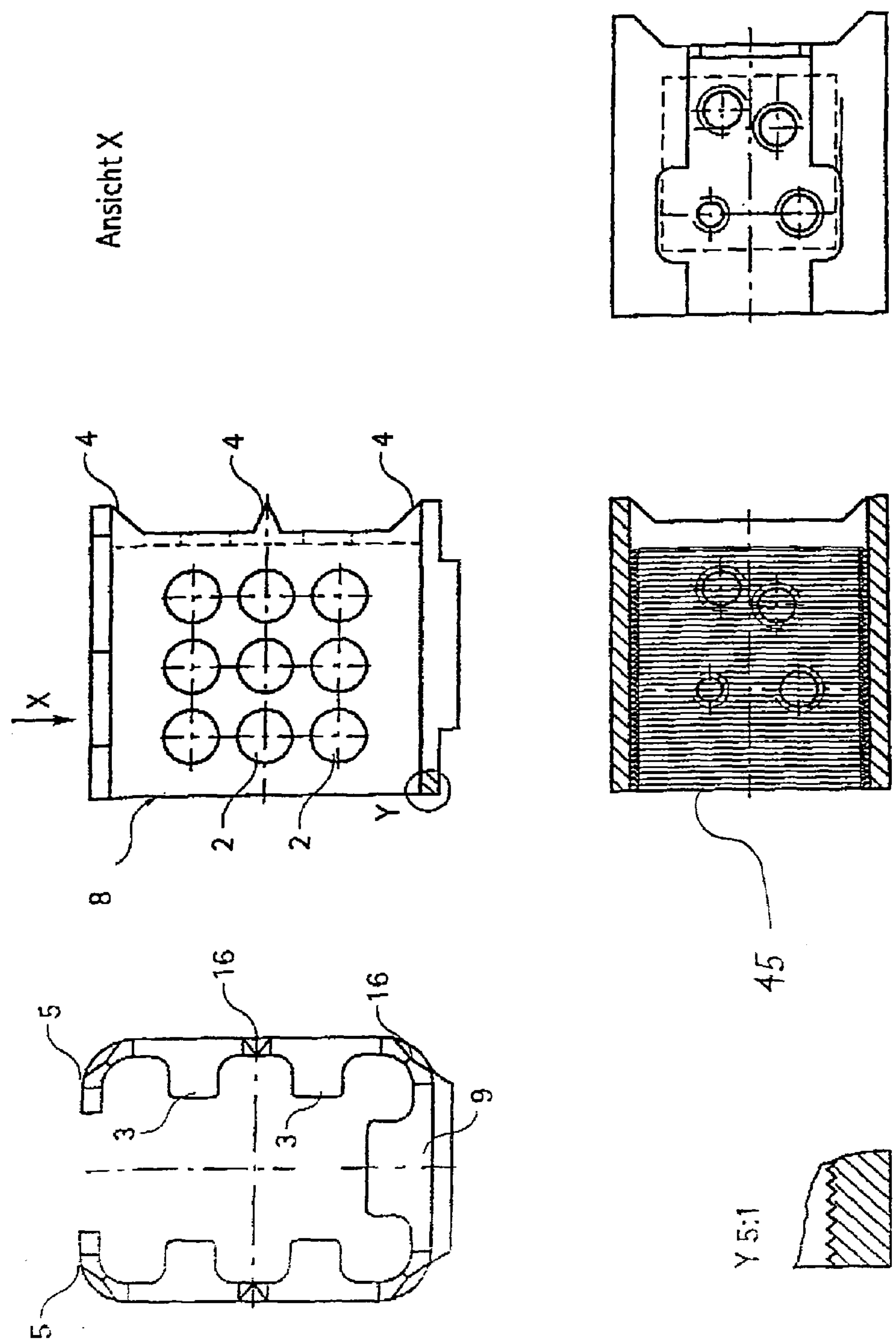
FIGS. 1; 2 a first embodiment of an outer cage and an inner cage in various views, and tongue-like vertebral support surfaces.

As can be seen from the Figures, the first inner cage 1 basically comprises recesses or break-throughs 2 provided in its legs. At the front face of the first inner cage 1, vertebral support surfaces 3 or webs 31, as well as tooth-like locking projections 4, are provided in an alternating manner extending in the longitudinal direction-relative to these support surfaces 3 or webs 31.

The locking projections can comprise a cutting edge 16 at their tips for facilitating the penetration into the respective opposite surface of the vertebra. On an inwardly directed curved portion 5, a recess (not shown) may be provided, which can be latched or clawed by means of bending with a tongue (not shown) of the outer cage 8.

As can be seen from the Figures, the area and the-shape of the implant have been optimized in such a manner that, for one, a small material amount is given and, for another, however, the mechanical stability meets the requirements, in particular the post-operative requirements. For example, the visible abutment edge 9, as well as the defined radii, too, which are obtained by a preferred treatment by way of milling or eroding, have a stability increasing effect. In the area of part 11 connecting the legs 10, a longitudinally extending elongated hole 12 including a toothing 13 is provided. A second elongated hole 14 is arranged essentially running in parallel and adjacent to the first elongated hole 12, and serves the purpose of locking the selected setting or adjustment position by means of a locking screw located in a thread bore of the second cage 8.

In the area of the curved portions, at or on the opposite surfaces of the first inner cage 1 and of the outer second cage 8, a toothing may be provided which effectively prevents an undesired displacement or rotation of the cages relative to each other.

Figure 2:
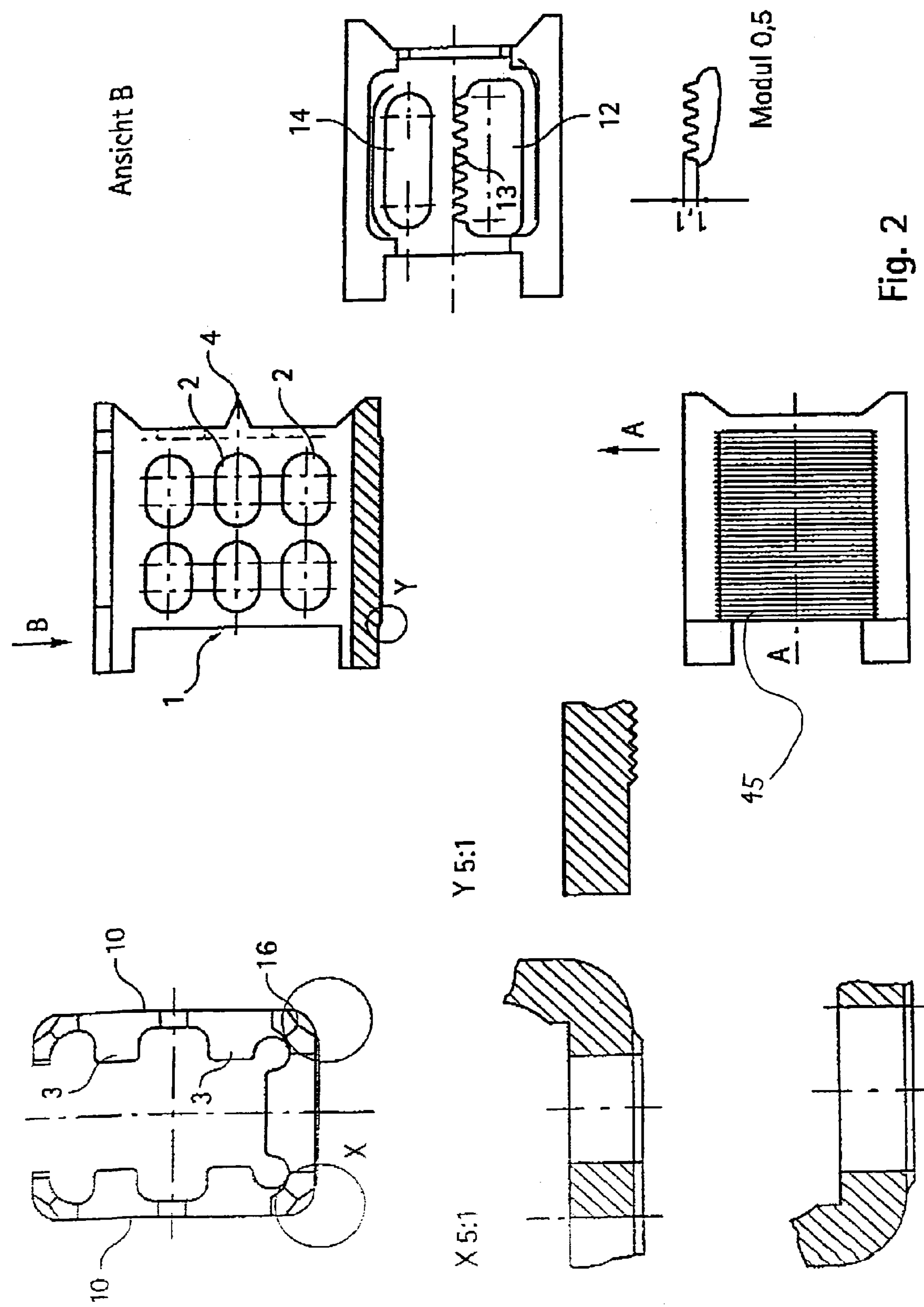

In FIGS. 1 and 2, the vertebral support surfaces 3 may be tongue-like and essentially opposite, with the interspaces exhibiting the mentioned locking projections 4. The lock-in toothing 45 is shown in FIGS. 1 and 2 as substantially perpendicular to the reference line A.

Figure 4:
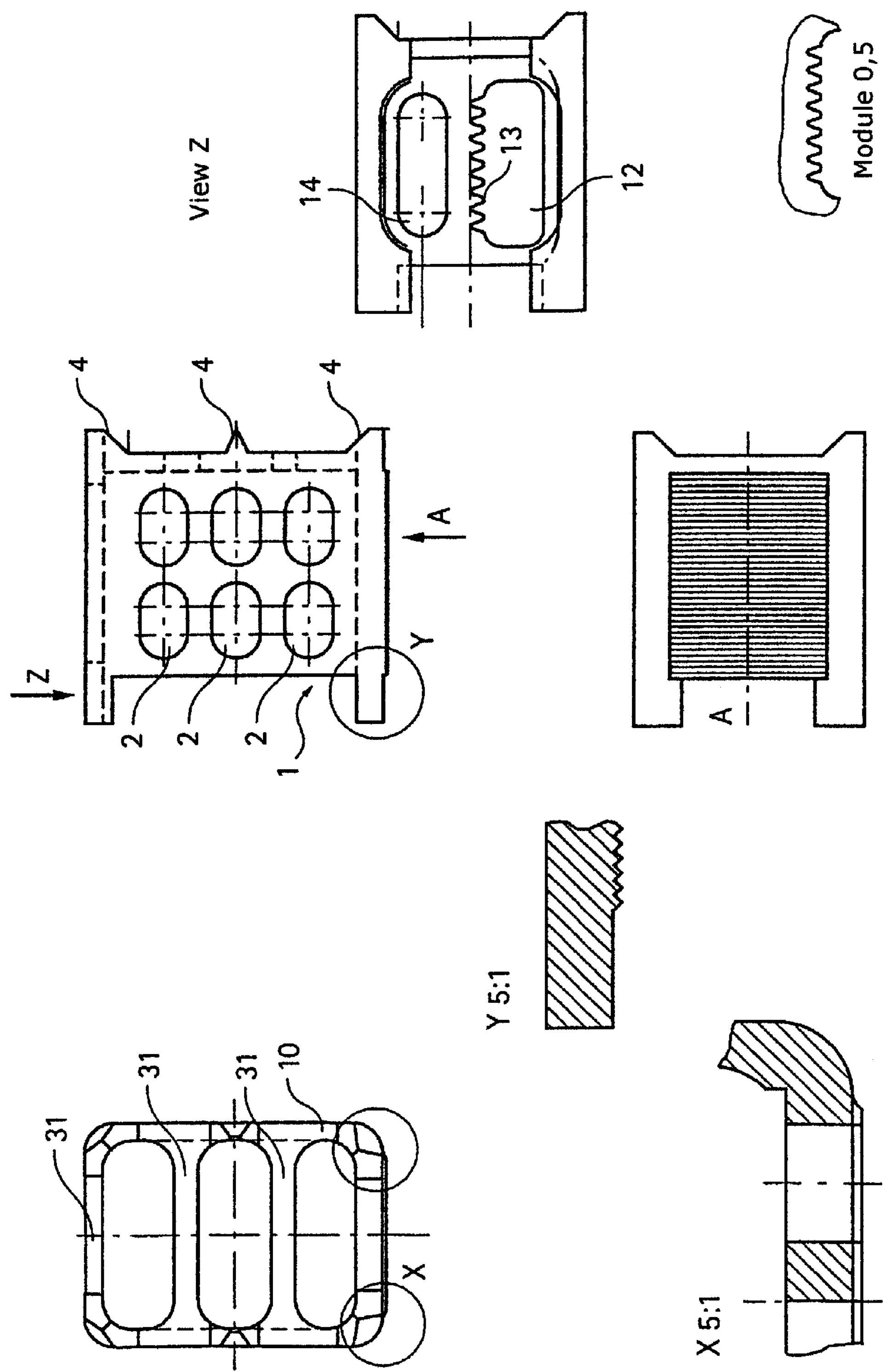

In the second exemplary embodiment as per FIGS. 3 and 4, webs 31 of a relatively small width are present instead of the tongues, whereby, for example, three webs in toto are assumed and one of the webs connects the two legs 10 on the opening side. The arrows 46 indicate that the webs may be of different widths.

Figure 5:
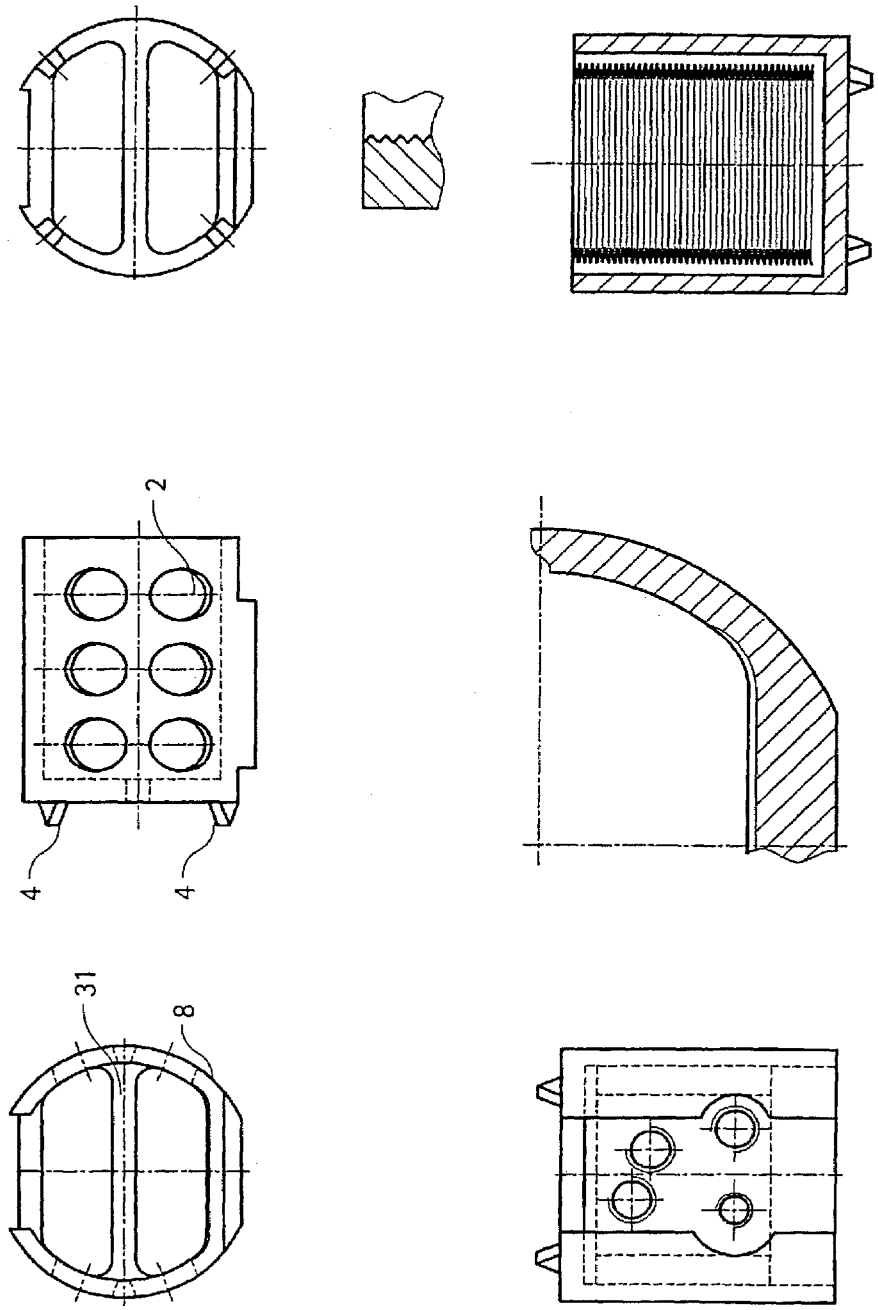
FIGS. 5; 6 a third embodiment, however, comprising a C-shaped outer cage and a C-shaped inner cage in various views, comprising webs as vertebral support surfaces.
Figure 6:
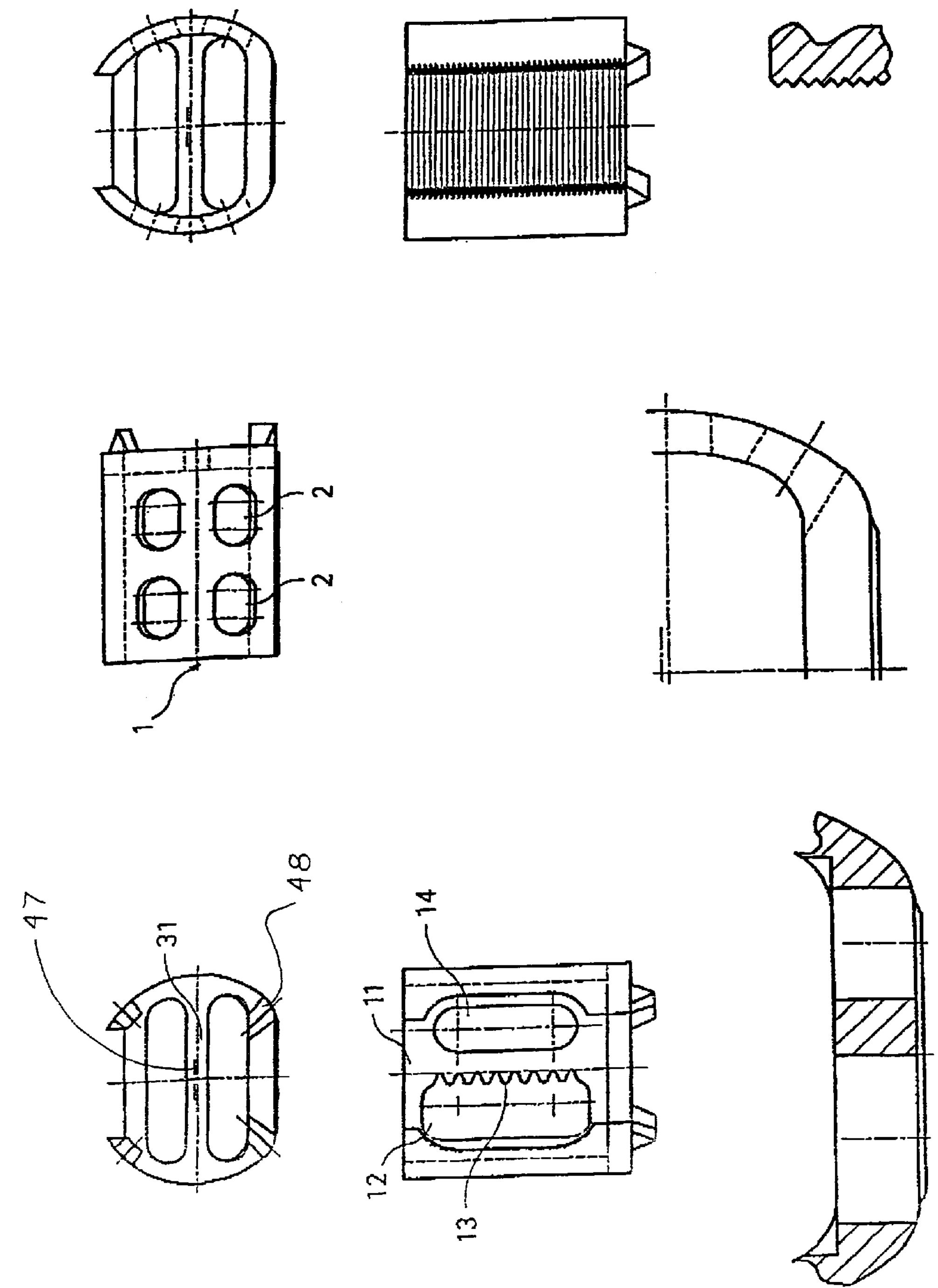

In the exemplary embodiment as per FIGS. 5 and 6, a C-shaped outer and inner cage, respectively are assumed. FIG. 6 also depicts a breaking point 47 and anchoring device 48.

The webs, for one, increase the stability of the cages against an undesired spreading apart and, for another, provide for the fact that the surface pressure towards the vertebral body is reduced or minimized.

Figure 7:
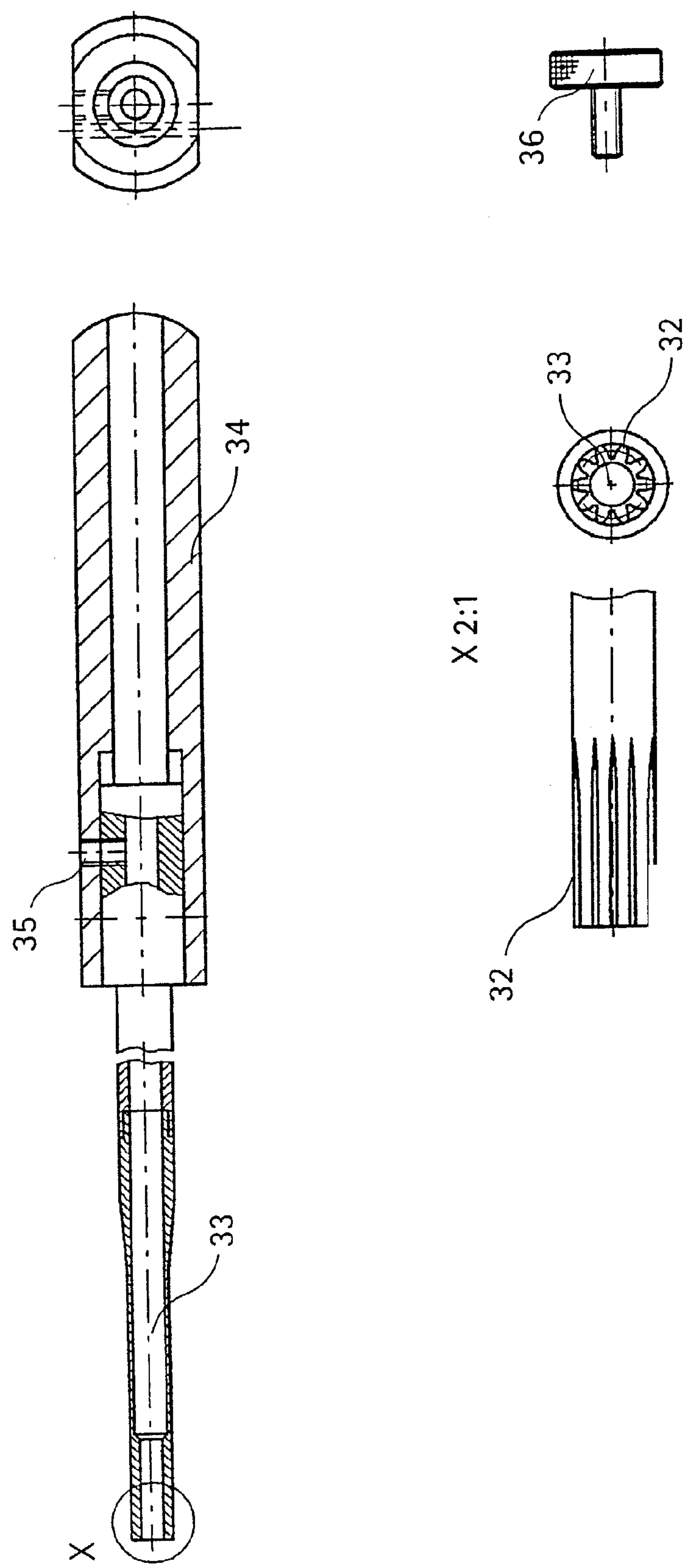
FIG. 7 a view of an instrument comprising an outer toothing.

The instrument shown in FIG. 7 has an outer toothing 32 configured to be complementary to the toothing 13 in the first elongated hole 12. Moreover, the instrument is may be provided in the nature of a hollow cylinder 33 and exhibits a handle 34 on its end opposite the outer toothing 32.

A bore 35 including a thread is in turn provided on the handle, which bore serves for receiving a knurled screw 36.

Figure 8:
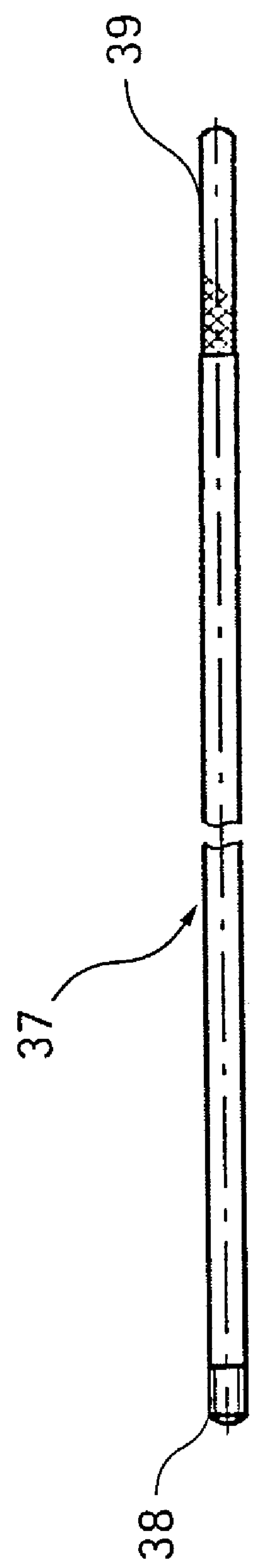
FIG. 8 a representation of the guidance rod.

A guidance rod 37 provided according to FIG. 8 has a thread end 38, as well as a knurled handling portion 39. The hollow cylinder 33 of the instrument having the outer toothing 32 and the outer diameter of the guidance rod 37 are mutually matched in such a manner that the instrument can be moved in the first elongate hole 12 quasi centered relative to the toothing 13.

Figure 9:
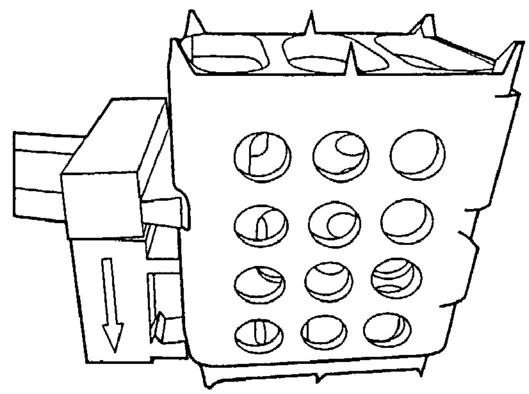
FIG. 9 representations for handling the gripping forceps.
Figure 9:
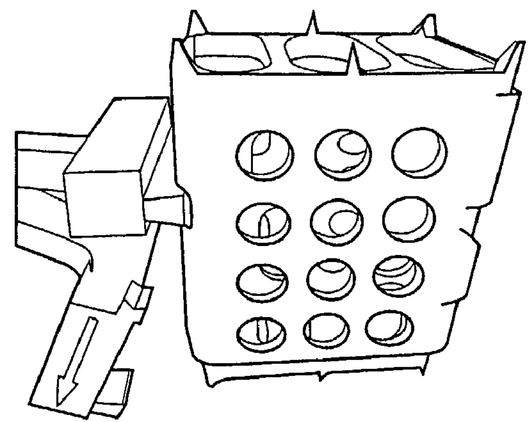
Figure 9:
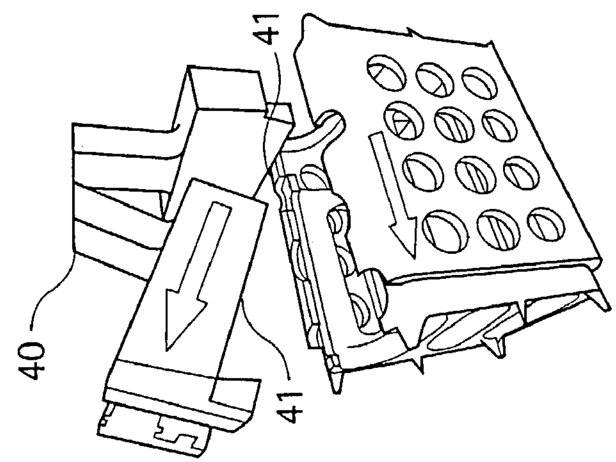

FIG. 9 shows in various views the lower zone of a gripping forceps 40 having clamping jaws 41. The arrow indicates the extension direction of the cage and hence the cranial implantation side, as well.

Figure 10:
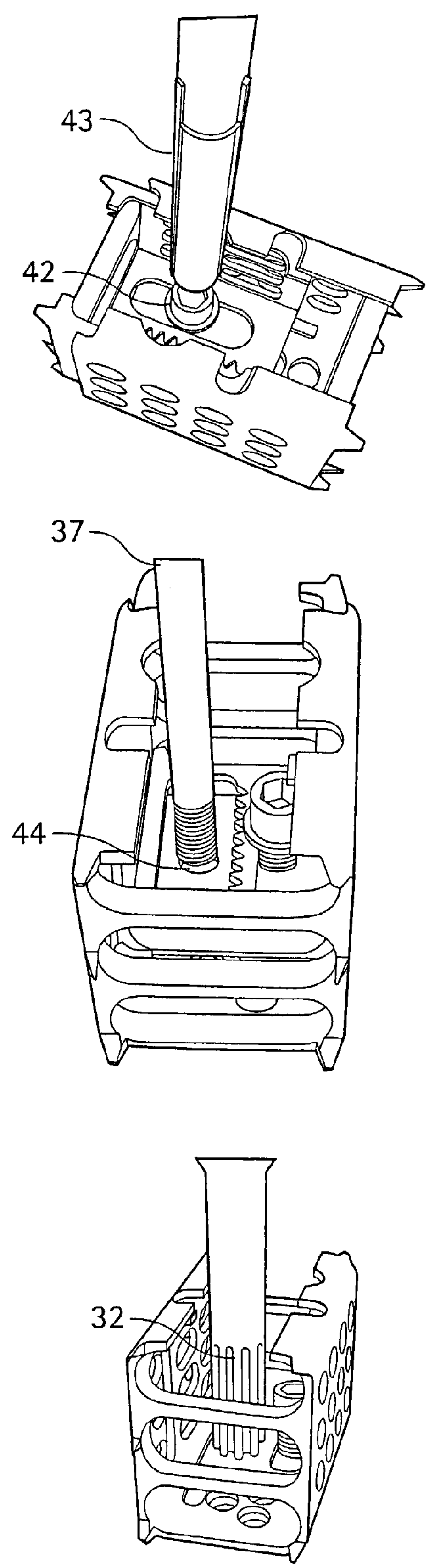
FIG. 10 representations for handling the actuating instrument set.

The upper image part as per FIG. 10 allows the recognition of the second elongated hole 14 with a therein inserted locking screw 42, and the lower portion of a screw driver 43. The locking screw 42 is loosely screwed in. According to the middle image as per FIG. 10, the guidance rod 37 is turned into the thread bore 44 that is situated in the outer cage below the zone of the elongated hole 12. Subsequently, as can be seen from the lower image part, the instrument having the outer toothing is slid over the guidance rod and is transported into a position where the outer toothing engages with the toothing 13 of the first elongated hole 12.

Figure 11:
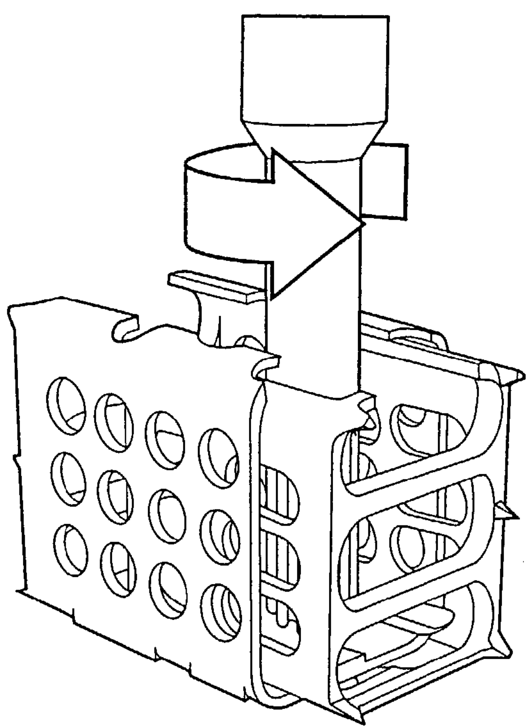
FIG. 11 representations for a height-adjustment by means of the instrument comprising the outer toothing.
Figure 11:
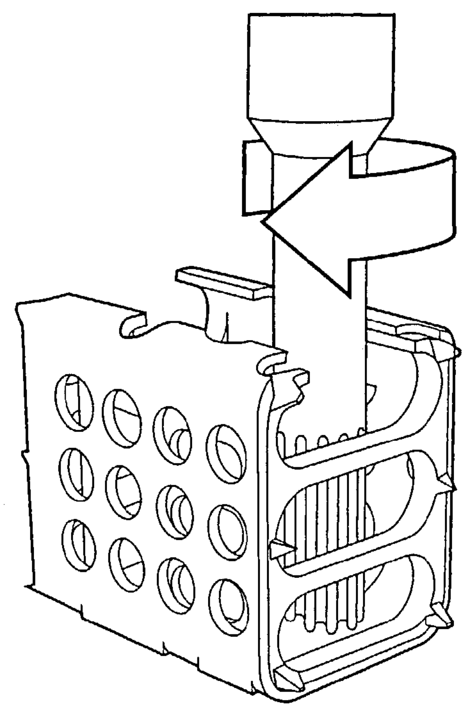

As can be seen from the representation as per FIG. 11, the inner cage can now be displaced relative to the outer cage in a translatory manner by turning the instrument having the outer toothing.

In summary, it is achieved with the proposed vertebral body implant to securely support the vertebral column without the amount of the foreign body material required for the supporting action exceeding a critical threshold. The manipulation of the implant itself is uncomplicated and essentially facilitated by the height-variability relative to the prior art. Due to the realization of the implant cages guided within each other from a metallic material machined by milling and/or eroding, the manufacture costs may be kept within limits.

LIST OF REFERENCE NUMERALS

1 inner cage
2 recesses, break-throughs
3 vertebral support surface
4 locking projections
5 curved portion
8 outer cage
9 abutment edge
10 leg
11 connecting part of the legs
12 first elongated hole
13 toothing
14 second elongated hole
16 cutting edge
31 webs
32 outer toothing
33 hollow cylinder
34 handle
35 bore in the handle
36 knurled screw
37 guidance rod
38 thread end
39 knurled handling portion
40 gripping forceps
41 clamping jaws
42 locking screw
43 screw driver
44 thread bore

The invention claimed is:

1. A height-variable vertebral body implant comprising:

a first, essentially U-shaped or C-shaped cage including vertebral support surfaces;

wherein the first cage is an inner cage, which is embraced and guided in a telescopic manner by a second, outer U-shaped or C-shaped cage including vertebral support surfaces, and wherein legs of the first and the second cages are aligned such that a continuous lateral opening is obtained, and the first and the second cages are configured to be mutually fixed in a predetermined final position, wherein at least one of frontal sides of each the first and second cages include at least one of the vertebral support surfaces and webs and tooth-like locking projections extending in a longitudinal direction, and the legs of the first and the second cages each comprise, on leg ends, an inwardly directed stability-increasing curved portion, with the first cage including an elongated hole extending in the longitudinal direction and including a unilateral toothing, wherein in cooperation with an instrument comprising a complementary toothing, a relative movement and an adjustment between the cages is effected.

2. The height-variable vertebral body implant according to claim 1, wherein at least in a zone of the curved portions, opposite surfaces of the first and the second cage comprise a lock-in toothing and a thread bore is formed in the second cage in a position below the zone comprising the elongated hole.

3. An actuating instrument set for a height-variable vertebral body implant according to claim 2, comprising a guidance rod having a thread end, the actuating instrument having a hollow cylinder with outer toothing and the hollow cylinder configured to receive the guidance rod and comprises on an end opposite the outer toothing a handle having a knurled screw acting upon the guidance rod.

4. The actuating instrument according to claim 3, further comprising a gripping forceps for gripping, orienting, or aligning the implant.

5. The actuating instrument according to claim 3, wherein for height-adjustment, the guidance rod is first inserted in the thread bore of the second cage, subsequently, the actuating instrument including the outer toothing is slid over the guidance rod, and rotatory movement is converted into a translatory movement by turning the handle and by an engagement of the toothing.

6. The actuating instrument according to claim 5, wherein by at least one locking screw, a given height position of the implant is preliminarily fixed on the actuating instrument to finally secure the height position thereafter with the at least one locking screw, for which purpose, a second thread bore is provided in the second cage, and a second elongated hole in the first cage is provided adjacent to the first elongated hole.

7. The height-variable vertebral body implant according to claim 1, wherein the tooth-like locking projections are ground to a cutting edge for facilitating penetration into the vertebral surfaces.

8. The height-variable vertebral body implant according to claim 1, wherein at least one of the webs and locking projections each provided on the frontal side of the first and second cages are arranged such that at least one of the webs is located between locking projections when viewed from the direction of the frontal side.

9. The height-variable vertebral body implant according to claim 1, wherein the cages are comprised of a metallic milled/eroded part.

10. The height-variable vertebral body implant according to claim 1, wherein the first and the second cages comprise a polygonal cross-section.

11. The height-variable vertebral body implant according to claim 1, wherein at least the first cage comprises recesses or break-throughs.

12. The height-variable vertebral body implant according to claim 1, wherein plural webs are provided running in parallel, forming support surfaces, and having different widths.

13. The height-variable vertebral body implant according to claim 1, wherein the webs are realized at least in part detachable and comprise predetermined breaking points to be detachable.

14. The height-variable vertebral body implant according to claim 1, wherein a material of the first and second cages has a residual elasticity for improved bone growth.

15. The height-variable vertebral body implant according to claim 1, further comprising an anchoring device configured to anchor on or in respective vertebral body surfaces.

16. A height-variable vertebral body implant system comprising:

a first essentially U-shaped or C-shaped cage including vertebral support surfaces;

wherein the first cage is an inner cage, which is embraced and guided in a telescopic manner by a second outer U-shaped or C-shaped cage including vertebral support surfaces, and wherein legs of the first and the second cage are aligned such that a continuous lateral opening is obtained, and the first and the second cages are configured to be mutually fixed in a predetermined final position, wherein at least one of frontal sides of each of the first and second cages include the vertebral support surfaces and webs and tooth-like locking projections extending in a longitudinal direction, and the legs of the first and the second cages each comprise, on leg ends, an inwardly directed stability-increasing curved portion, with the first cage including an elongated hole extending in the longitudinal direction and including a unilateral toothing, and an actuating instrument including a hollow cylinder with a first end with toothing configured to mate with the unilateral toothing and a second end with a handle, a guidance rod with a threaded end and configured to fit into the hollow cylinder, a knurled screw configured to act upon the guidance rod through the second end of the hollow cylinder, wherein the actuating instrument is configured to move one cage with respect to the other cage.

* * * * *